United States Patent [19]

Soo

[11] Patent Number: 5,028,595

[45] Date of Patent: Jul. 2, 1991

[54] METHOD FOR PREVENTING AIDS IN A SUBJECT OR TREATING A SUBJECT INFECTED WITH THE AIDS VIRUS

[75] Inventor: Whaijen Soo, Wyckoff, N.J.

[73] Assignee: Hoffmann-La Roche Inc., Nutley, N.J.

[21] Appl. No.: 396,197

[22] Filed: Aug. 21, 1989

Related U.S. Application Data

[63] Continuation of Ser. No. 98,255, Sep. 18, 1987, abandoned.

[51] Int. Cl.$^5$ ............................................. A61K 31/70
[52] U.S. Cl. ...................................... 514/49; 514/934
[58] Field of Search ................................. 514/49, 934

[56] References Cited

U.S. PATENT DOCUMENTS

| | | | |
|---|---|---|---|
| 4,879,277 | 11/1989 | Mitsuya | 514/49 |
| 4,963,533 | 10/1990 | de Clereq | 514/49 |

FOREIGN PATENT DOCUMENTS

| | | |
|---|---|---|
| 596864 | 3/1988 | Australia . |
| 593405 | 6/1988 | Australia . |
| 0206497 | 12/1986 | European Pat. Off. . |
| 216510 | 4/1987 | European Pat. Off. . |
| 216511 | 4/1987 | European Pat. Off. . |

OTHER PUBLICATIONS

Balzarini Molecular Pharmacology, 32, No. 1, Jul. 1987, pp. 162–167.
Herdewjn et al., J. Med. Chem. 30:1270–1278, 1987.
Kim et al., Chem. Abst., 106:156808n, 1987.
Mitsuya et al., Chem. Abst., 104:183216h, 1986.

*Primary Examiner*—John W. Rollins
*Attorney, Agent, or Firm*—George M. Gould; Bernard S. Leon; William H. Epstein

[57] ABSTRACT

A method for treating a subject infected with the AIDS retrovirus without substantial neuropathy by administering 2′,3′-dideoxycytidine to the subject at a dose of from 0.001 to 0.05 milligram per kilogram per day.

5 Claims, No Drawings

METHOD FOR PREVENTING AIDS IN A SUBJECT OR TREATING A SUBJECT INFECTED WITH THE AIDS VIRUS

This is a continuation of application Ser. No. 07/098,255, filed Sept. 18, 1987, abandoned.

BACKGROUND OF THE INVENTION

The field of viral chemotherapeutics has recently developed in response to the particularly challenging problems presented with respect to the diagnosis and treatment of viral diseases. Of particular interest is the development of compounds effective against retroviruses, most particularly the HIV virus.

The effectiveness of any antiviral chemotherapeutic naturally depends on many factors including the identification of the specific virus, an understanding of its infectivity, life cycle, replication, and spread within the infected host.

All viruses must replicate and transcribe their nucleic acids into messenger RNA which in turn translates into proteins for progeny virions. For DNA viruses, the virus synthesizes its own DNA polymerase enzyme which uses the cell's supply of purines and pyrimidines to make additional copies of the viral DNA.

Retroviruses are characterized in that they are able to synthesize DNA from the RNA template which comprises their genetic material via a polymerase enzyme "reverse transcriptase" and are therefore characterized as retroviruses. This DNA, which corresponds to the RNA version of the viral genome, is then incorporated into the host cell genome and viral DNA is synthesized in the course of the normal host cell processes. The HIV virus is characteristically a retrovirus and possesses the enzyme reverse transcriptase.

Antiviral compounds with various modes of action are known in the art. For example, a class of compounds known as nucleoside analogs exhibit broad antiviral activity by interfering with the viral life cycle.

These "fraudulent" nucleosides (or 2',3' dideoxy derivatives) are analogs of the normal DNA or RNA building blocks; adenosine, thymidine, cytidine, guanosine or uridine. However, unlike their normal counterparts these compounds cannot be used in normal DNA or RNA synthesis. In the cell these fraudulent nucleosides deceive the virus into thinking they are normal DNA or RNA building blocks. The "fraudulent" counterpart is utilized in the viral life cycle ultimately resulting in viral suicide.

Unfortunately, most of these antiviral substances which are nucleoside analogs are not specific inhibitors of only viral processes. Most of these compounds will interfere to a greater or lesser degree with normal molecular processes of the host cell resulting in toxic effects on uninfected cells.

This is particularly true with the 2',3' dideoxynucleoside analogs such as 2',3' dideoxycytidine (ddC) and the analogs thereof. ddC in particular causes peripheral neuropathy which results in tingling, numbing and pain which may require potent pain killers such as morphine when administered at the dosages which are effectively antiviral.

In the case of a 2',3' dideoxyadenosine particularly high dosages are necessary to be effectively antiviral.

SUMMARY OF THE INVENTION

The instant invention comprises the discovery that extremely low dosages of dideoxynucleoside analogs exhibit no neuropathic effects yet are effective in preventing AIDS or treating subjects infected with the AIDS retrovirus.

By dideoxynucleoside analogs is meant any 2',3'-dideoxy analog of adenosine, thymidine, cytidine, guanosine, uridine or inosine wherein two hydroxy substituents are absent from the 2' and 3' positions on the ribose portion of the nucleoside molecule. Included are 2',3'-dideoxynucleoside radicals where the nucleoside is substituented with amino, halogen, alkyl, azido, cyano, and other groups commonly found on nucleoside analogs. Also within the scope of this invention is the use of acyl and phosphate esters of the 5'-hydroxy group.

DETAILED DESCRIPTION

The instant invention comprises preventing AIDS in a subject or treating a subject infected with the AIDS virus by administering to the subject from 0.001 to 0.10 mg/kg/day of a dideoxynucleoside analog.

Preferred is where the dideoxynucleoside analog is 2',3'-dideoxycytidine.

Particularly preferred is wherein 0.001 to 0.05 mg/kg 2',3'-dideoxycytidine is administered to a subject in one to six doses per day.

Most preferred is wherein 0.01 mg/kg 2',3'-dideoxycytidine is administered four times a day to a subject.

The compound may be administered orally, intravenously, parenterally, or mucocutaneously.

It is possible for the compounds of the present invention to be administered alone in solution. However, in the preferred embodiment, the active ingredient(s) may be used or administered in a pharmaceutical formulation. These formulations comprise at least one active ingredient (the dideoxynucleoside), together with one or more pharmaceutically acceptable carriers and/or other therapeutic agents. As included within the scope of this invention, "acceptable" is defined as being compatible with other ingredients of the formulation and not injurious to the patient or host cell. These carriers include those well known to practitioners in the art as suitable for oral, rectal, nasal, topical, buccal, sublingual, vaginal, or parenteral (including subcutaneous, intramuscular, intravenous, and intradermal) administration. Specific carriers suitable for use in the invention are further defined below. With reference to the utilization of a pharmaceutically acceptable derivative. In the present case, it will be appreciated that the compounds according to the invention may also be used in the manufacture of pharmaceuticals for the treatment or prophylaxis of viral infections.

The formulations may conveniently be presented in unit dosage form and may be prepared by any methods known in the pharmaceutical art. Such methods include the preparation of the active ingredient in a carrier which may contain additional medicinally active ingredients.

One method of oral administration of the 2',3'-dideoxycytidines of the present invention consists of dissolving an effective amount of the 2',3'-dideoxycytidine in a sodium chloride solution, preferably 0.9% sodium chloride in orange juice. The preferred method is administration of the 2',3'-dideoxynucleosides in tablet form, and may include one or more of the following: lactose (hydrous, fast flow), microcrystalline cellulose, colloidal silicon dioxide, croscarmellose sodium, magnesium stearate, stearic acid, and other excipients, colorants, and pharmacologically compatible carriers. Compositions for oral use may be administered to patients in fasting or non-fasting state. Examples of tablet formulations are indicated in Tables 1 and 2.

Formulations of the present invention suitable for oral administration (including sustained release formulations) may be presented as discrete units such as capsules, cachets or tablets, each containing a predetermined amount of the active ingredient; as a powder or granules; as a solution or a suspension in an aqueous liquid; in an oil-in-water liquid emulsion or a water-in-oil liquid emulsion. The active ingredient may also be presented.

Formulations suitable for topical administration include lozenges comprising the active ingredient in a flavor, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising, for example, cocoa butter or a salicylate.

Formulations suitable for vaginal administration may be presented as pessaries, tampons, creams, gels, pastes, foams; or spray formulas containing in addition to the active ingredient such carriers as are known in the art to be appropriate.

Formulations suitable for parenteral administration include aqueous and non-aqueous, isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

The administered ingredients may also be used in therapy in conjunction with other anti-viral drugs and biologicals, or in conjunction with other immune modulating therapy including bone marrow or lymphocyte transplants or medications.

What is claimed is:

1. A method for treating a subject infected with the AIDS retrovirus without substantial neuropathy comprising administering 2',3'-dideoxycytidine to the subject at a dose of from 0.001 to 0.05 milligram per kilogram per day.

2. The method of claim 1, wherein said 2',3'-dideoxycytidine is administered orally or intravenously.

3. The method of claim 2, wherein said 2',3'-dideoxycytidine is administered orally.

4. The method of claim 3, wherein said 2',3'-dideoxycytidine is administered at a dose of 0.05 milligram per kilogram per day.

5. The method of claim 4, wherein the 2',3'-dideoxycytidine is administered four times a day.

* * * * *